United States Patent [19]

Sainz

[11] Patent Number: 4,615,225
[45] Date of Patent: Oct. 7, 1986

[54] IN-SITU ANALYSIS OF A LIQUID CONDUCTIVE MATERIAL

[75] Inventor: Mario A. Sainz, Londonderry, N.H.

[73] Assignee: Allied Corporation, Morristown, N.J.

[21] Appl. No.: 711,350

[22] Filed: Mar. 13, 1985

[51] Int. Cl.$^4$ .......................... G01N 1/10; G01N 1/14
[52] U.S. Cl. .............................. 73/864.33; 73/863.11; 73/DIG. 9; 356/36
[58] Field of Search ......... 73/DIG. 9, 863.11, 864.33, 73/863, 864; 356/36, 313; 313/231.01

[56] References Cited

U.S. PATENT DOCUMENTS

| | | | |
|---|---|---|---|
| 3,460,393 | 8/1969 | Putnam | 73/DIG. 9 |
| 3,572,124 | 3/1971 | Nagaoka et al. | 73/DIG. 9 |
| 3,602,595 | 8/1971 | Dahlquist et al. | 356/313 X |
| 3,606,540 | 9/1971 | Williams et al. | 356/313 |
| 3,645,628 | 2/1972 | Bojic et al. | 356/313 |
| 3,659,944 | 5/1972 | Bojic | 356/313 |
| 3,669,546 | 6/1972 | Virloget | 356/313 |
| 3,672,774 | 6/1972 | Bojic et al. | 356/313 |
| 3,974,698 | 8/1976 | Scott, Jr. | 73/DIG. 9 |

FOREIGN PATENT DOCUMENTS

| | | | |
|---|---|---|---|
| 1066039 | 9/1957 | Fed. Rep. of Germany | 356/313 |
| 157539 | 9/1984 | Japan . | |
| 157540 | 9/1984 | Japan . | |
| 157541 | 9/1984 | Japan . | |
| 157542 | 9/1984 | Japan . | |
| 157543 | 9/1984 | Japan . | |
| 135648 | 3/1961 | U.S.S.R. | 356/313 |

OTHER PUBLICATIONS

"Direct Analysis of Liquid Metal: A Technique Ahead of Its Time", *Iron and Steel International*, vol. 52, No. 2, pp. 77–83, A. Wittmann.

*Primary Examiner*—Stewart J. Levy
*Assistant Examiner*—Tom Noland
*Attorney, Agent, or Firm*—Paul Zee; Lowell McCarter; Gerhard Fuchs

[57] ABSTRACT

A method and apparatus for measuring the constituent elements of a liquid, electrically conductive material includes a probe housing, which delimits a sampling chamber constructed to contain a non-reactive gas, and includes an entry mechanism for introducing aliquot of the liquid material into the sampling chamber. An inner housing is located within the probe housing and is moveable longitudinally relative thereto. A housing adjustment mechanism selectively positions the inner housing longitudinally relative to the probe housing. A spark electrode is disposed within the inner housing and is in communication with the sampling chamber. This electrode is longitudinally moveable relative to the inner housing and is constructed to spark an electrical arc discharge between the spark electrode and the free surface of the liquid aliquot, thereby producing a aerosol sample composed of particles of the material in the gas. A spark electrode adjustment mechanism selectively positions the spark electrode longitudinally relative to the inner housing to selectively locate an electrical discharge portion of the spark electrode farther from the liquid free surface than from the sampling end portion of the inner housing. A gas entry mechanism provides an atmosphere of non-reactive gas at a selected pressure in the sampling chamber and provides a flow of the gas through the inner housing, through the region of the electrical arc and through the sampling chamber. An exit mechanism directs a flow of the gas and the aerosol sample out from the sampling chamber.

13 Claims, 15 Drawing Figures

IN-SITU ANALYSIS OF A LIQUID CONDUCTIVE MATERIAL

BACKGROUND OF THE INVENTION

1. Field of the Invention

The invention relates to a method and apparatus for measuring the constituent elements of a liquid conductive material. More particularly, the invention relates to measuring the constituent elements of a melt of molten metal alloy.

2. Description of the Prior Art

The physical properties of metal alloys, such as strength, hardness, toughness and corrosion resistance, depend in part upon the composition of the metal. In particular, these properties depend on the quantities of the constituent alloying elements.

To determine the composition of the alloy, a liquid sample is typically drawn from a melt of the molten alloy, allowed to solidify and then analyzed by chemical or spectrometric means. When the analysis indicates the correct composition, the melt is poured to produce the desired products. Efficient production requires a rapid and accurate analysis because continuing chemical processes in the melt can change the composition between the time the sample is drawn and the time the analysis is received. If the time separation is too great, the analysis may not accurately represent the true composition of the melt.

Attempts have been made to provide accurate "real-time" analyses of molten metal alloys. U.S. Pat. No. 3,659,944 issued May 2, 1972 to M. Bojic discloses an apparatus for the direct and continuous spectrometric measurement of molten metals. U.S. Pat. No. 3,645,628 issued Feb. 29, 1972 to M. Bojic et al. provides an apparatus for direct spectrometric analysis of molten metals which has a light conveying tube with a disposable tubular extension. U.S. Pat. No. 3,672,774 issued June 27, 1972 to Bojic et al. provides an apparatus for direct spectrometric examination of molten metals.

U.S. Pat. No. 3,669,546 issued June 13, 1972 to J. M. Virloget disclosure a special optical transmission apparatus which receives light generated by a spark between an electrode and the surface of a molten metal. The apparatus transmits the light with minimum alteration to a spectrographic means.

The spark emission measurement devices of the prior art, however, have many shortcomings. The spark is an inefficient producer of light emissions because the spark absorbs much of the radiation. As a result, the linear dynamic range of the emissions produced is rather short. A further disadvantage of a spark emission analytical technique is the requirement that the sampled melt surface be free of slag and representative of the bulk material. A critical parameter is the geometry of the melt surface and counter electrode. In particular, the gap length, or distance between the counter electrode and melt surface, should remain, at all times, substantially constant. Dynamic changes in gap length can impair the analytical accuracy and precision of the results. The spark emission procedure also produces matrix effects because the material eroded from the electrodes interferes with the light emissions from the excited sample. Since the emitted light must be conducted to a spectrometer, the light becomes scattered and attenuated by intervening atmospheric molecules and by the transmission mirrors and lenses used in the optical systems. This necessitates close placement of the spectrometer near the molten metal and the use of special, complex optics to conduct the light.

Typically, the prior art devices pump molten metal to a sampling point, or take the sample from near the melt surface where the slag can interfere with the analysis. Such procedures are not conducive to obtaining precise insitu analyses. The spark emission devices also produce residual vapors that can interfere with later samples and analyses, and the devices are unable to provide data on the melt composition at varied locations and depths in the melt to ascertain its homogeneity.

U.S. Pat. No. 3,606,540 issued Sept. 20, 1971 to R. V. Williams, et al. uses a gas stream to atomize a molten metal. The molten droplets in the form of a spray are conducted by a stream of gas through a tube conduit to a plasma spectrometer. The spectrometer analyzes the droplets, and a special gas barrier formed in the conduit is intended to keep the metal droplets away from the tube walls. The atomizer-type device of Williams, et al., however, has not been completely satisfactory. The gas automizer droplets are generally too large for efficient transport by a flowing gas. Droplets can still solidify on the transport tube walls and clog the tube. Also, residue from prior samples can interfere with the analysis of subsequent samples.

U.S. Pat. No. 3,602,595 to R. L. Dahlquist discloses a device which creates an electric arc between an anode of a current source and a material to be sampled. The arc creates an aerosol containing droplets of the material, and the aerosol is carried away by a flow of gas for spectrometric analysis. U.S. Pat. No. 3,685,911 issued Aug. 22, 1972 to R. L. Dahlquist, et al. provides an apparatus for producing a stabilized arc plasma in a capillary tube. Material introduced into the plasma is excited to produce light emissions, and these light emissions are analyzed by spectrometer.

The device taught by Dahlquist, however, has not been able to produce reliable or consistently reproducible analyses of a molten material. The surface of the liquid melt ripples and moves, making it difficult to maintain the spark gap required to consistently produce a sufficient quantity of aerosol particles from the spark for analysis.

Thus, conventional devices, such as those discussed above, have been unable to efficiently provide accurate and reliable real-time analyses of molten metals. Spark devices have been inefficient producers of emissions for spectrometric measurement, and these spark systems have required complicated optics to transmit the light to the spectrometer for analysis. Atomization systems have been susceptible to clogged transport tubes, and new samples have been often contaminated by residue left behind by previous samples. Spark devices, which produce an aerosol for subsequent spectrometric analysis, however, have not been able to reliably produce an aerosol from a molten sample that contains a sufficient concentration of particulates for accurate analysis. The electrical arc sometimes caused movement and displacement of the liquid without providing any analytical signal. The intensities of the analytical signal, when present, would greatly fluctuate over time and these fluctuations would unacceptably decrease the precision of the analysis. In addition, material from the liquid being sampled could contaminate the spark electrode and inhibit further analyses.

SUMMARY OF THE INVENTION

The invention provides method and apparatus for rapidly, efficiently and accurately measuring the constituent elements of a liquid, electrically conductive material.

Generally stated, the apparatus includes a probe housing which delimits a sampling chamber constructed to contain a non-reactive gas, and includes an entry means for introducing an aliquot of the liquid material into the sampling chamber. An inner housing is located within the probe housng and is moveable longitudinally relative thereto. Housing adjustment means selectively position the inner housing longitudinally relative to the probe housing. A spark electrode is disposed within the inner housing and is in communication with the sampling chamber. The electrode is longitudinally moveable relative to the inner housing and is constructed to spark an electrical arc discharge between the spark electrode and a free surface of the liquid aliquot, thereby producing an aerosol sample composed of the gas and particles of material from the aliquot. Spark electrode adjustment means selectively position the spark electrode longitudinally relative to the inner housing to selectively locate an electrical discharge portion of the spark electrode farther from the liquid free surface than from a sampling end portion of the inner housing. Gas entry means provide an atmosphere of non-reactive gas at a selected pressure in the sampling chamber, and provide a flow of the gas through the inner housing, through the region of the electrical arc and through the sampling chamber. Exit means direct a flow of the gas and the aerosol sample out from the sampling chamber.

The invention further provides a method for sampling a liquid, electrically conductive material which includes the step of positioning an inner housing at a selected longitudinal location within a probe housing. A spark electrode is positioned at a retracted position within the inner housing, thereby spacing an electrical discharge portion of the spark electrode inward from a sampling end portion of the inner housing by a first selected distance. An aliquot sample of the liquid material is introduced into a sampling chamber, which is delimited by the probe housing and which is in fluid communication with the inner housng sampling portion and the spark electrode. An atmosphere of non-reactive gas at a selected pressure is provided in the sampling chamber, and a reference liquid level is detected. At the reference liquid level, the location of a liquid free surface of the aliquot is substantially the same as the location of the inner housing sampling end portion. A relative distance between the liquid free surface and the inner housing sampling end portion is changed to establish a separation position at which the inner housing sampling portion is removed and spaced from the liquid free surface by a selected separation gap. The spark electrode within the inner housing is positioned at a work position spaced inward from the sampling end portion of the inner housing by a selected working distance. An electrical arc is sparked between the spark electrode and the free surface of the liquid aliquot, thereby producing an aerosol sample composed of particles of the material in the gas. A flow of the non-reactive gas is provided through the sampling chamber and through the region of the electrical arc. A flow of the non-reactive gas and the aerosol sample are directed out from the sampling chamber.

The longitudinally moveable inner housing advantageously allows the inner housing to be set at a location spaced inward from the end of the probe housing at a distance which can be optimized for the particular liquid being sampled. The longitudinally moveable spark electrode allows the electrode to be positioned at a retracted location which minimizes contamination of the electrode when the probe is being inserted into the liquid material. In addition, the moveable spark electrode allows a positioning of the electrode at a spark gap distance which can be optimized for the particular liquid material being sampled.

The configuration of an aerosol-generating probe in fluid communication with a remotely located analyzer means is particularly advantageous for the real-time, quantitative analysis of the constituent elements in materials such as molten metals or corrosive liquids. Manufacturing processes involving these materials often occur in environments that are extremely hostile to the sensitive electronics and mechanisms of spectrometers and computers. For example, it would be impractical to provide the air-conditioning required by a computer located near a steel furnace. In addition, spectrometers and/or light conveyance optics typically require clean optical surfaces. Molten metals can generate particles that condense on these surfaces and degrade their performance. The apparatus of the invention, however, can locate the analyzer means over a hundred feet from the selected volume of liquid appointed for analysis.

In conventional elemental emission analysis systems, the single emissive discharge is called upon to abalate (or otherwise remove sample material), disperse, desolvate, atomize, ionize, and spectrally excite atoms from the sample. The invention, advantageously provides separated sampling and excitation steps, and as a result, is able to minimize interfering matrix effects. In addition, the independent control of the sampling and excitation steps allows an optimization of each of the steps. Since the linear dynamic range of intensities of radiant emissions produced by an inductively coupled plasma is significantly larger than the linear dynamic range of emissions produced by sparks, the invention has a greater effective range over which concentrations can be measured. The present invention also avoids the use of complex optics to transmit light to a remotely located spectrometer by instead, generating an aerosol sample and then transporting it to a remotely located exciter means. The aerosol sample can be transported distances of several hundred feet without clogging the transport tubes, and new samples are substantially uncontaminated by prior samples.

In addition, the present invention is capable of providing and maintaining a selected spark gap distance between the liquid to be sampled and the spark electrode, and is capable of providing a controlled flow rate and flow velocity in the region of the electric arc. These factors improve the ability of the invention to reliably produce aerosol samples that are capable of providing consistent, high intensity signals when analyzed by spectrometric analyzers.

The invention includes a maneuverable sampler probe which advantageously can be located at selected depth locations in the melt, thereby avoiding the top layer of slag and providing accurate in-situ measurements to determine the composition and homogeneity of the melt. Since the associated spectrometer can be remotely located without optical couplings, it can be more conveniently set and operated.

Thus, compared to conventional spark emission and gas atomizer types of devices, the invention more efficiently and more accurately analyzes in-situ samples of conductive liquids, such as molten metal alloys. Samples from varied locations within the liquid can be rapidly analyzed to provide real-time information on the liquid's composition and homogeneity, thereby allowing more precise control of these factors.

This invention, when coupled with suitable hardware for achieving automatic alloy additions, an optical pyrometer for temperature measurements, and computer hardware and software for controlling each of these individual processes, can allow a complete automation of the overall metal making process. Composition measurements obtained with the invention would be employed to determine the nature and quantity of metallurgical component additions. For example, in steel making, the combined thermal and composition measurements could determine the rate and manner in which oxygen is introduced into the BOF (Basic Oxygen Furnace) melt. The potential benefits of this process include the reduction of energy, materials, and labor costs while at the same time ensuring improvements in product quality.

BRIEF DESCRIPTION OF THE DRAWINGS

The invention will be more fully understood and further advantages will become apparent when reference is made to the following detailed description of the preferred embodiment of the invention and the accompanying drawings in which.

DESCRIPTION OF THE PREFERRED EMBODIMENTS

While the preferred embodiments of the invention are described in context of analyzing molten metal alloys, it is readily apparent that the invention can be used to analyze any electrically conductive liquid. For example, plating baths can be continuously monitored and additions can be made to maintain the proper concentrations of materials in the bath. Also, when refining bauxite with sodium fluoride to produce metallic aluminum, the slurry can be monitored to maintain the optimum ratio of sodium to aluminum. All of such applications are contemplated as being within the scope of the invention.

Figure 1:
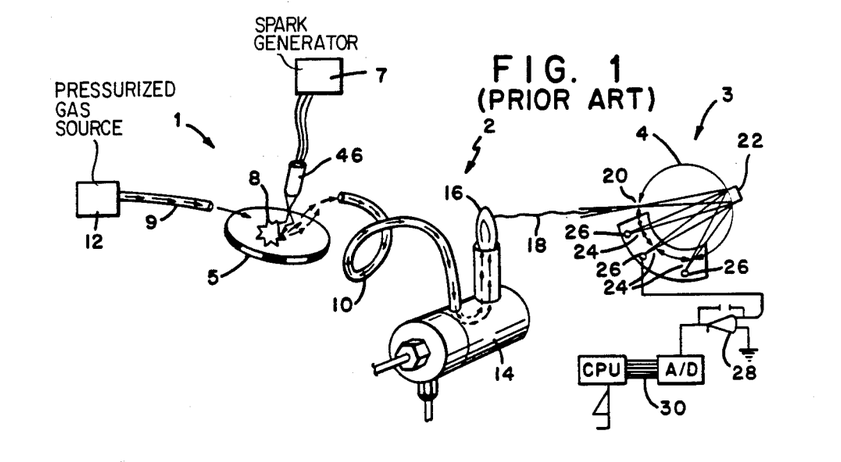
FIG. 1 shows a schematic representation of a spectrometric analysis system.

Referring to FIG. 1 of the drawings, there is illustrated a schematic representation of a prior art analyzer apparatus comprised generally of a sampler means 1 and an analyzer means. The analyzer means includes an exciter means 2 and detector means 3. Detector means 3, in turn, includes a spectrometer 4 and a computer processor 30.

Sampler means 1 has a spark generator means 7 operably connected to spark electrode 46. A nonreactive gas, such as argon gas, is delivered from pressurized gas source 12 to sample 5 through a suitable conduit 9 to provide a desired atmosphere. Thereafter, spark generator 7 arcs a spark between sample 5, a conductive material 8, and electrode 46. The spark erodes small particles from the sample to form an aerosol sample in the argon gas. This aerosol sample will contain elements at the concentrations found within sample 5. The pressurized argon gas then transports the aerosol sample through conduit 10 to the analyzer means for excitation by exciter means 2 and measurement by spectrometer 4.

Figure 2:
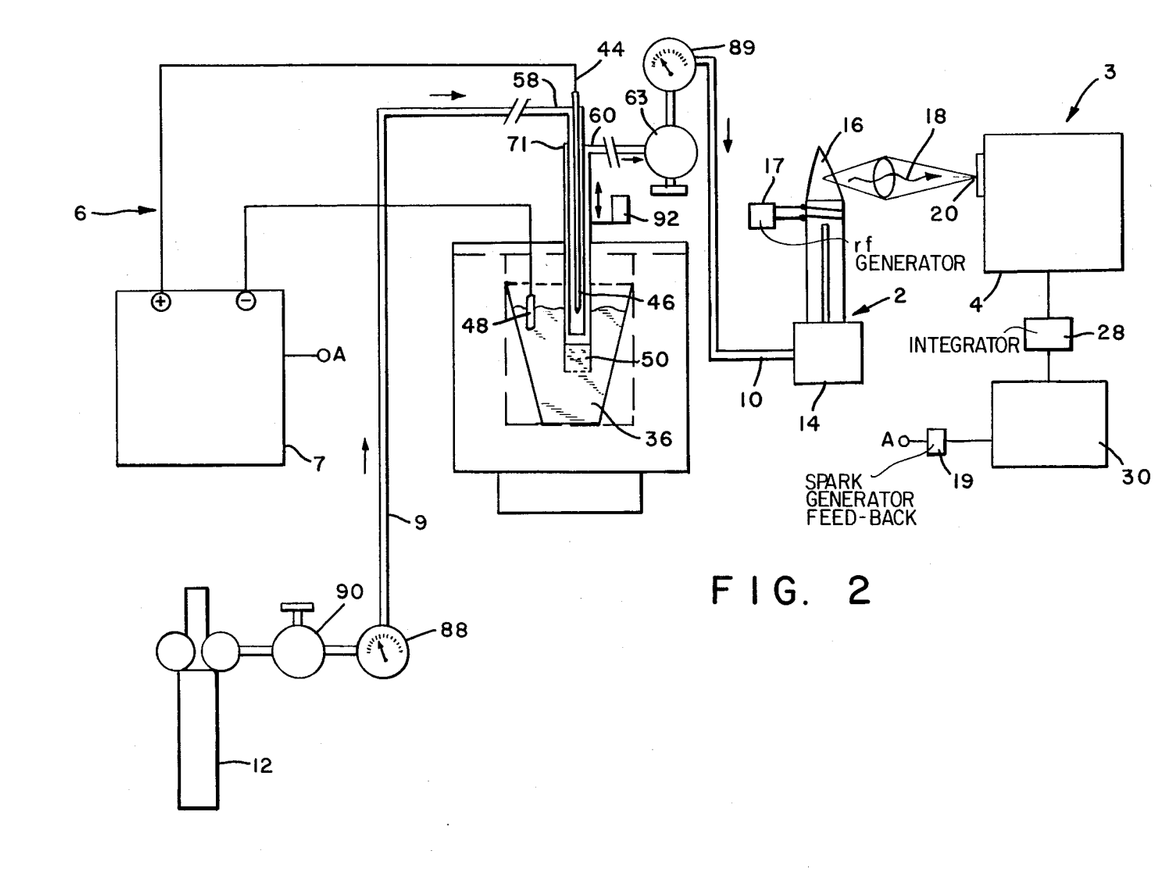
FIG. 2 shows a schematic representation of the apparatus of the invention.

FIG. 2 shows a schematic representation of the apparatus of the invention. The components of the invention are similar to the prior art analyzer apparatus except that the spark electrode 46 is now contained inside a probe 71 and sample 5 is replaced by a sample aliquot 50 composed of a conductive liquid. Probe means 71 is capable of being inserted into the conductive liquid material, such as molten metal 36, to define an aliquot volume 50 thereof within the probe. A non-reactive gas, such as argon or helium, is delivered from pressurized gas source 12 through conduit 9 to provide a non-reactive gas atmosphere over the aliquot sample. Regulator 90 controls the gas pressure and flow rate through conduit 9, and monitor 88 monitors the pressure and flow rate provided to probe 71. An optional regulator 63 can control the gas pressure and flow rate through conduit 10, and an optional monitor 89 can monitor the pressure and flow rate provided between probe 71 and exciter 2. In a preferred aspect of the invention, the melt density and sampling depth are employed to determine an operating pressure chosen via regulator 90. The flow rate at exciter 2 is determined by a limiting orifice in the system; for example, a limiting orifice located in conduit 9, probe 71, or conduit 10.

Sampler means 6 ablates, erodes or otherwise produces an aerosol of very fine particles within the non-reactive gas. Pressurized flow of the gas transports the aerosol through fluid conduit 10 to a remotely located analyzer means comprised of exciter means 2 and detector means 3. The exciter means excites the material in the aerosol particles to produce characteristic emission spectra which are analyzed by detector means 3 comprised of spectrometer 4 and computer 30.

Sampling means 6 is preferably comprised of a spark generator 7 and an associated electrode 46 within the probe. However, it is readily apparent that other means such as lasers, ion beams, radio wave beams, microwave beams or ultrasonic sound devices, may also be employed with probe 71 to produce the desired aerosol particles composed of elements at the concentrations found within aliquot 50.

Exciter means 2 excites the particles, such as by heating, causing the particles to radiate atomic emission spectra characteristic of the constituent elements therein. The characteristic frequencies of emitted radiation (emission spectra) identify the constituent elements, and the intensities of the radiation indicate the quantities thereof. In the shown embodiment, the aerosol sample is directed from probe 71, through conduit 10 and optional chamber 14, and into an inductively coupled plasma torch 16 driven by rf generator 17. The plasma torch excites the atoms within the aerosol sample to radiate characteristic emission spectra 18 which are then detected by detector means 3.

Detector means 3 is remotely located with exciter means 2, and is comprised of spectrometer means 4 and computer processor means 30. In the shown embodiment, radiation enters entrance slit 20 of spectrometer 4, and the various spectral frequencies are separated and spread by a reflection-type diffraction grating 22 (FIG. 1). The separated frequencies of radiation pass through exit slits 24 and enter intensifiers, such as photomultiplier tubes 26, which amplify the various signals produced by the incoming spectra. The amplified output signals are integrated with integrator means 28 and processed by computer 30 to provide a readout of the constituent elements in melt 36 and the quantities thereof. Preferably, computer 30 also comprises a feedback means 19 for controlling the spark intensity of sampler means 1.

When preparing a melt of molten metal alloy, it is important to quickly and accurately monitor the composition of the melt because the melt composition substantially determines the physical properties, such as strength, hardness, toughness, corrosion resistance and fatigue resistance of the solid metal. As raw materials are introduced into the melt, precise quantities of alloying elements and innoculants must be added to maintain the desired melt composition. Therefore, a precise analysis of the melt is needed to determine the amount of additional alloying elements and innoculants required. The in-situ sampling probe of the invention is especially suited for rapidly and efficiently taking samples of material from various locations within the melt. The probe can be maneuvered to selected locations and depths and can rapidly sample a chosen volume of molten metal.

Figure 3:
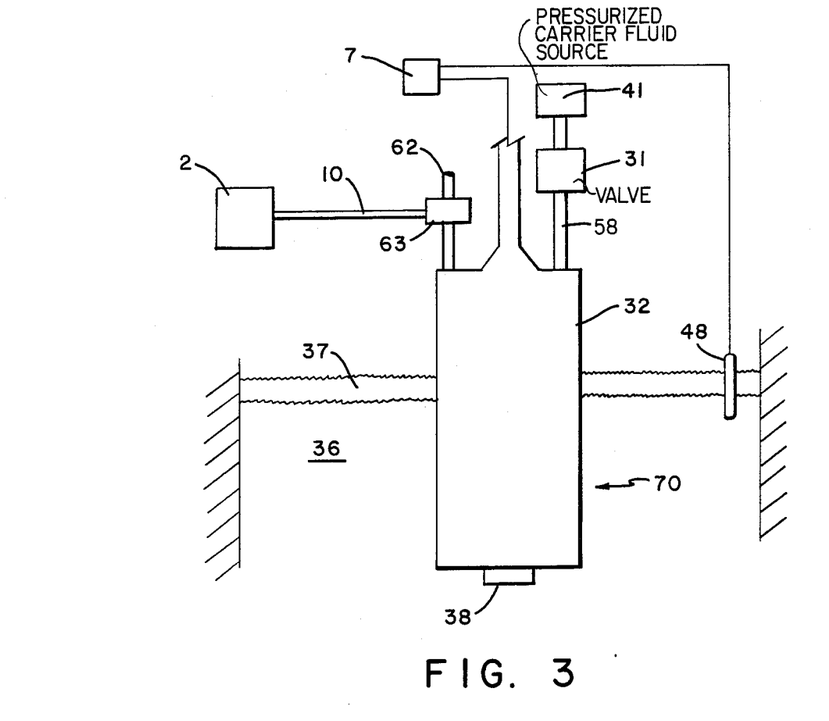
FIG. 3 shows a schematic representation of the in-situ probe of the invention.
Figure 4:
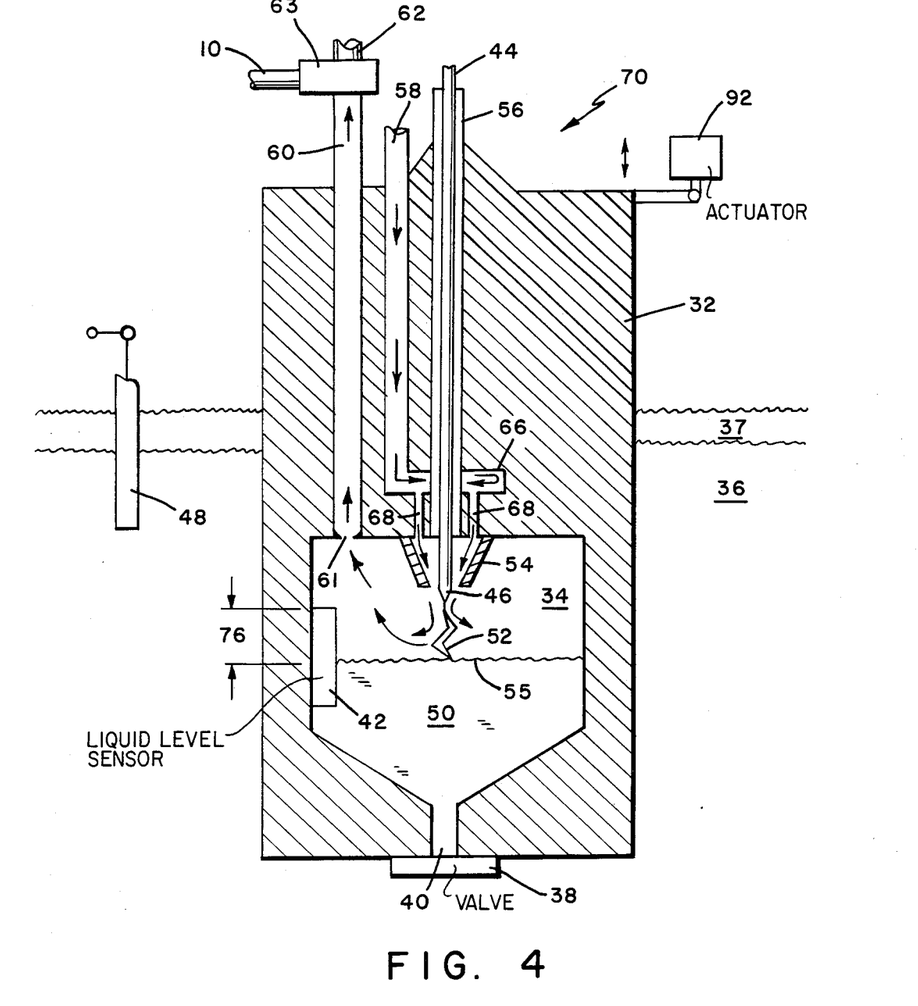
FIG. 4 shows a schematic longitudinal cross-sectional view of the probe of the invention.

FIGS. 3 and 4 show a more detailed illustration of the sampling probe of the invention, generally at 70, wherein an elongated probe housing 32 delimits a sampling chamber 34. Gas supply means comprised of conduit 58, annulus 66, ports 68 and nozzle 54 provide an atmosphere of nonreactive gas in chamber 34; and an entry means, comprised of orifice 40 and optional valve 38, introduces conductive material into the sampling chamber. Gap setting means, such as liquid level sensor/detector 42 and actuator 92, measures and selectively sets a selected spark gap distance between a free surface 55 of the liquid and spark electrode 46. Electrode 46 may also be referred to as a counter electrode. Pressure control means, such as valve 31, control the pressure of the non-reactive gas to maintain a substantially constant spark gap distance 76 between spark electrode 46 and the liquid free surface 55. Spark electrode 46 and ground electrode 48 are constructed and arranged to arc an electrical spark between spark electrode 46 and the free surface 55 of the volume of the conductive material introduced therein. This spark produces an aerosol sample of the material in the gas. Pressure means 41 then moves and flows the gas in the region of electric arc 52 at a flow velocity which is sufficient to sweep the aerosol particles away from liquid aliquot 50. The flowing gas then transports the aerosol sample out of chamber 34 to exciter means 2 of the analyzer means. The analyzer means then analyzes the aerosol sample to measure the constituent elements of the liquid conductive material.

Probe housing 32 is composed of a material resistant to the temperature and corrosive action of the particular liquid being analyzed. In a probe for molten metal, housing 32 is preferably constructed of a non-corroding, high melting point metal, such as stainless steel, or a refractory material, such as alumina ($Al_2O_3$) or quartz.

Electrical power lead 44 extends through housing 32 and connects to spark electrode 46 which, in turn, is operably located in chamber 34. Lead 44 is isolated from the probe housing by an electrical insulator 56, and a ground electrode 48 is adapted to form an operable electrical contact with the liquid contained therein. Electrodes 46 and 48 then operably connect to spark generator 7 through suitable electrical leads.

Pressurized non-reactive gas, such as argon, helium or neon, enters housing 32 through conduit 58, passes through annulus 66 and then enters chamber 34 through ports 68 and nozzle 54 to provide the non-reactive atmosphere in chamber 34. By adjusting the size of gas outlet opening 61 and by controlling the gas pressure with suitable control means, such as valve 31, the inert gas can also regulate the level of liquid within chamber 34. The inert gas flows out of chamber 34 through orifice 61 and conduit 60, and is then selectively directed by valve 63 through conduit 62 to purge the system or through conduit 10. Gas flow directed through conduits 60 and 10 provides an exemplary transport means for moving the aerosol sample from chamber 34 to exciter means 2. An optional valve 38 controls the entry of molten metal through orifice 40 into chamber 34, and a level sensor 42, disposed within chamber 34, detects the level of liquid therein. Preferably, however, liquid flow through orifice 40 is controlled by the pressure of the inert gas in chamber 34.

During sampling operations in a melt of molten metal, pressurized non-reactive or inert gas flows through nozzle 54 into chamber 34 and exits the chamber through both orifice 40 and opening 61. An initial high pressure burst of gas flow at about 20 l/min and 40 psi pressure is directed by valve 63 through conduit 62 to purge the system of residual material that might interfere in the analysis. After purging, gas flow is reduced and directed by valve 63 through conduit 10. Probe 70 is inserted through the top layer of slag 37 into melt 36 of the molten metal alloy, and is selectively located at a desired depth and position within the melt by a suitable positioning means. During this positioning period, the gas pressure is adjusted to exceed the metallostatic pressure head of the melt, thereby preventing metal or slag from entering chamber 34. Once probe 70 is located as desired, the gas pressure in chamber 34 is reduced allowing a submerged, subsurface volume of liquid metal to enter chamber 34 through orifice 40. This provides an aliquot 50 of material within the chamber. Gap reference means, comprised of level sensor 42, detects the liquid level which defines the gap separation between spark electrode 46 and the liquid surface level 55. When the appropriate spark trigger level is reached, spark generator 7 applies a high voltage, ranging from about 12-17 KV, between electrodes 46 and 48 to spark an arc (i.e. electrical discharge) 52 between electrode 46 and the liquid surface 55. Arc 52 erodes material from surface 55 thereby creating an aerosol sample of the metal alloy within the inert gas. A flow of inert gas transports the aerosol through orifice 61, and conduits 60 and 10 conduct the aerosol to the plasma in exciter means 2. To enable efficient transport of the aerosol over long distances by means of gas flow, the aerosol particulates should be about 0.1 micrometers in size or less. The method and apparatus of the invention advantageously provides aerosol particulates ranging from about 4-100 nanometers in diameter.

The particular gas flow rate is selected to produce an injection rate matched to the requirements of the specific exciter means 2. For example, where the exciter and spectrometer are comprised of a Model 86-632 manufactured by Jarrell Ash of Waltham, MA, the preferred gas flow rate ranges from about 0.6 to 1 l/min (liters per minute).

Radiant emission spectra from the excited sample of material are processed by spectrometer 4 and computer 30 to determine the constituent elements of the sample and the quantities thereof. An analysis readout is available within about 60 seconds. Preferably, computer 30 is operably connected to provide a feedback signal which controls the spark generator and the trigger level in chamber 34. This feedback regulates the spark gap separation between electrode 46 and surface 55 to optimize the intensity of spark 52.

As a result of evaporation and chemical reactions, the composition of the melt is dynamic during the metal making process. Thus, as time elapses, aliquot 50 in chamber 34 may no longer by representative of melt sample 36. To assure proper sample representation, additional aliquots should be taken from melt sample 36 at frequent intervals. A new aliquot 50 is obtained by raising the pressure in probe 71 sufficiently to force the old aliquot out from chamber 34 back into the bulk melt 36; the original gas pressure is then reinstated in probe 71. This allows a new aliquot 50 to enter into chamber 34 and reestablish a gap 76 which remains substantially unaltered with respect to the previously set spark gap.

Figure 5:
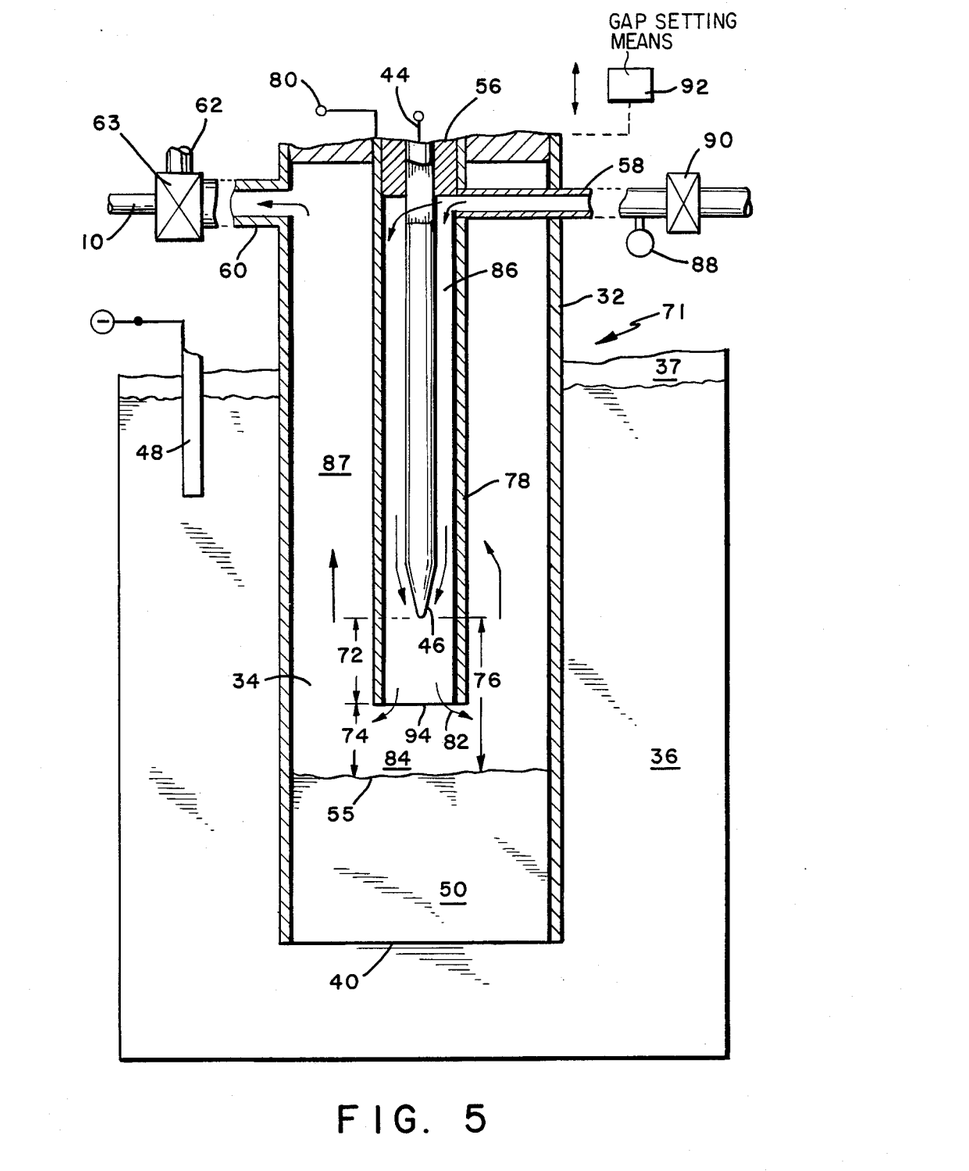
FIG. 5 shows a schematic cross-sectional view of another probe.

FIG. 5 representatively shows a schematic cross-sectional view of a particularly advantageous probe configuration, which is a further aspect of the invention. Probe 71 includes an outer probe housing 32, which delimits sampling chamber 34 and preferably has a tubular, cylindrical shape. Chamber 34 has spark (counter) electrode 46 disposed in communication therewith and is constructed to contain a non-reactive gas. Opening 40 located at one end of housing 32 provides an entry means for introducing an aliquot 50 of conductive liquid 36 into chamber 34.

Spark electrode 46 is disposed in communication with sampling chamber 34 and is arranged to spark an electrical arc (i.e. discharge) between electrode 46 and a free surface 55 of liquid aliquot 50. The arc produces an aerosol sample composed of particles of the conductive material in the non-reactive gas.

Inner housing 78 is rigidly and fixedly located within probe housing 32 and positioned substantially concentric with probe housing 32 and spark electrode 46. The tubular inner housing is located around electrode 46, and has an open end portion 94, which communicates with sampling chamber 34. Electrical insulation 56 isolates electrode 46 from housing 78, and holds the electrode in fixed relation with respect to the inner housing. Inner housing 78 also extends down closer to aliquot 50 than electrode 46 by a selected distance 72.

A gas entry means is comprised of a conduit 58 which communicates into annulus region 86. The gas entry means provides an atmosphere of non-reactive gas at a selected pressure in sampling chamber 34, and provides a flow of the gas through inner housing 78, through the region 84 of the electrical arc and into sampling chamber 34.

The particular configuration of electrode 46 and inner housing 78 provides an accurate reference means for detecting a reference gap distance 72 between electrode 46 and free surface 55 of the liquid aliquot. During operation, gas enters inner annulus 86 to provide a selected pressure in inner housing 78 and sampling chamber 34, and probe 71 is inserted down into melt 36. At a certain depth into the melt, surface 55 will have risen to touch inner housing end portion 94 and will block off the flow of gas coming from inner housing 78. The initial stoppage of flow indicates that the gap between electrode 46 and surface 55 is equal to A "default gap" distance 72. The precise depth at which gas flow stoppage occurs is a function of the pressure in annulus 86 and the density of melt 36. For a given melt (liquid) composition, the depth at which gas flow blockaqe occurs can be readily calculated by a person having ordinary skill in the art and can be varied by regulating the incoming gas pressure with regulator 90.

Once the reference gap is detected, a gap setting means 92 selectively changes the separation between electrode 46 and surface 55 from the reference, "default," gap to a selected spark gap distance 76. Gap setting means 92 is, for example, comprised of an actuator mechanism which selectively moves probe 71 up and down in the direction of the arrows. The amount of upward movement needed to increase the gap by additional distance 74 and provide spark gap 76 is, again, a function of the gas pressure in inner housing 78 and the density of melt 36. The required amount of movement, however, can be readily calculated by a person skilled in the art. The vertical translational movement of probe 71 advantageously sets spark gap 76 without having to calibrate precise gas pressures needed to produce desired spark gap settings. In a preferred embodiment of the invention, spark gap 76 ranges from about 3-5 mm. In any case, the optimum spark gap setting, which provides the most stable and useable signal intensity from a plasma exciter, can depend upon the particular composition of the liquid being sampled.

A flow control means for controlling the flow of the gas in the region 84 of the electrical arc is comprised of the regulated gas pressure supplied to annulus 86, the separation gap distance 74, the configuration of the gas entry means into housing 78 and the regulated flow rate out through exit conduit 60. Together these elements provide a flow velocity 82 which is sufficient to gather and sweep the aerosol particles away from surface 55 and liquid aliquot 50.

A transport and exit means is comprised of an outlet conduit 60, which communicates with chamber 34 through outer annulus 87. This transport means directs a flow of gas and the aerosol sample out from sampling chamber 34. A flow of gas through conduit 10 moves and conducts the aerosol to an analyzer means.

A further aspect of the invention is a probe configuration which produces a turbulent gas flow through inner housing 78 and through arc region 84. In particular, entry conduit 58 is offset radially, toward one side of inner housing 78 and selectively angled to provide a tangential component of gas flow into the inner housing. As a result, the entering gas flow develops a swirling, circumferential velocity component with respect to housing 78. The swirling gas travels longitudinally through housing 78, through arc region 84, and efficiently collects aerosol particles generated by the spark to sweep them away from aliquot 50 toward exit tube 60. The operation of the gas flow is particularly efficient when the flow velocity 82 out and around end portion 94 is at least about 10 cm/sec.

In still another aspect of the invention, the gas pressure in sampling chamber 34 is selectively controlled during the insertion of probe 71 into the melt. The sampling chamber pressure is adjusted to reduce the gas flow through the chamber while probe 71 is being moved to establish the reference gap position. Reducing the sampling chamber gas pressure can advantageously reduce bubbling of gas through the melt, reduce agitation or spattering of liquid material within sampling chamber 34, and allow a more accurate setting of the probe to the reference gap position. After extended periods of spark generation and sampling, the spark anode can become contaminated and begin to produce erratic quantities of aerosol samples. Consequently, the intensity of the analytic signal from the spectrometer also becomes erratic. To remove the anode contamination and reacquire the desired stability in the signal intensity, probe 71 is moved from the spark gap setting to another larger gap setting, and a spark is generated from the anode. This procedure can effectively remove the contamination. Thereafter, probe 71 is reset to the desired spark gap to begin sampling again. In an alternative procedure, contamination may be removed from the spark anode by reversing the polarity of the electrical power supplied to the probe and producing a spark within the probe with the modified power. The resultant reversed direction of current flow can then remove the contamination.

Figure 12:
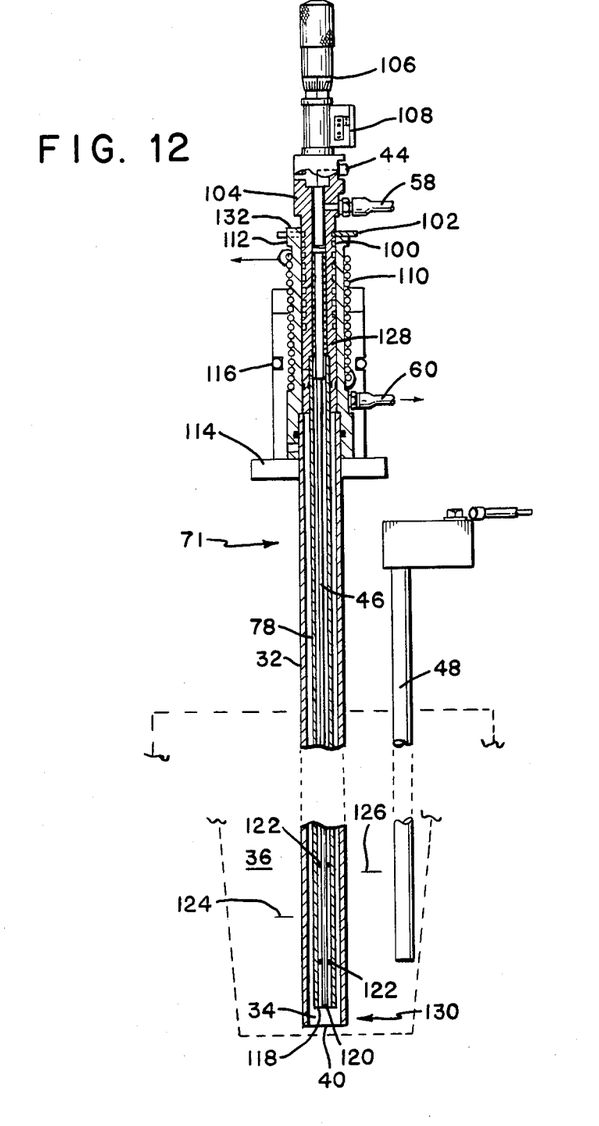
FIG. 12 representatively shows a longitudinal cross-sectional view of a probe configuration of the invention which has an adjustable inner housing and an adjustable spark electrode.

FIG. 12 representatively shows a schematic cross-sectional view of a further embodiment of the invention. Sampling probe 71 includes an outer probe housing 32 which delimits sampling chamber 34 at a bottom, distal end portion 130 thereof. An entry means comprised of opening 40 introduced an aliquot of liquid material 36 into sampling chamber 34. Inner housing 78 is located within probe housing 32 and is moveable longitudinally relative thereto. A housing adjustment means comprised of probe housing support 112 and C-retainer washer 102 selectively positions inner housing 78 longitudinally relative to the axial length of probe housing 32. Spark electrode 46 is disposed within inner housing 78 and is in communication with sampling chamber 34. Electrode 46 is longitudinally moveable relative to inner housing 78 and is constructed to spark an electrical arc discharge between spark electrode discharge portion 120 and a free surface of the liquid aliquot. This produces an aerosol sample composed of particles of the material within a non-reactive gas contained in chamber 34. A spark electrode adjustment means, such as micrometer adjustment 106 selectively positions spark electrode 46 longitudinally along the axial length of inner housing 78 to selectively locate an electrical discharge portion 120 of electrode 46 farther from the liquid free surface than from a sampling end portion 118 of inner housing 78. A gas entry means, such as conduit 58, provides an atmosphere of the non-reactive gas at a selected pressure in sampling chamber 34. The gas entry means further provides a flow of gas through inner housing 78, through the region of the electrical arc and through sampling chamber 34. Exit means, such as conduit 60, directs a flow of the gas and the aerosol sample out from chamber 34.

In a prefered embodiment of the invention, probe housing 32 and inner housing 78 are configured as hollow cylindrical tubes. In addition, inner housing 78 is located substantially concentric with probe housing 32 and with spark electrode 46.

Probe housing 32 includes a probe housing support member 112 which is rigidly attached to an axial end portion there of. Support member 112 is constructed to mount in a probe carrier 114. A retainer spring mechanism 116 holds support member 112 substantially fixed within carrier 114. Housing support 112 and carrier member 114 are composed of a suitable material such as brass or stainless steel. A tubular metal coil 110 is helically coiled around housing support 112 and is constructed to conduct a fluid coolant, such as water. Cooling coil 110 minimizes excessive temperature rise within probe 71.

Inner housing 78 is slideable longitudinally relative to outer probe housing 32 and includes a top support portion 132 which is extendable past a terminal end 104 of probe housing support 112. Top portion 104 has a plurality of substantially parallel circumferential grooves 100 formed therein. A clamping means, such as C-retainer clip 102 selectively engages the probe housing support and at least one of the grooves 100 to hold the inner housing in a selected, substantially constant position with respect to probe housing 32.

An electrode adjustment means includes a screw-drive mechanism, such as micrometer 106, which is connected to spark electrode 46 and constructed to slideably move the electrode longitudinally relative to the axial length of inner housing 78. A measuring means, such as digital readout 108, indicates the relative longitudinal position between spark electrode 46 and inner housing 78. More particularly, the measuring means indicates the relative longitudinal separation gap between the electrode spark discharge portion 120 and the sampling portion 118 of inner housng 78.

A porous or perforated member 122 allows the passage of gas therethrough and helps keep spark electrode 46 centered within inner housing 78. In a particular embodiment of the invention, the upper-most (inner-most) position of inner housing 78 places end portion 118 about 2 inches inward from the open end 40 of probe housng 42. In addition, the upper-most position of spark electrode 46 places the spark discharge portion 120 of electrode 46 about 0.75 inches inward from the open end 40 of inner housing 78.

In another aspect of the invention, probe housing 32 is composed of an electrically conductive, silicon carbide (SiC) refractory material. Suitable material is available from Kanthal Furnace Products, Bethel, Conn. When the probe housing is composed of silicon carbide, the separate ground electrode 48 can be eliminated; the silicon carbide probe housing 32 can function as the ground electrode when appropriately connected to the power source provided by spark generator 7.

Advantageously, the apparatus of the invention can quickly and efficiently analyze the composition of a molten metal at various locations and depths within the melt. To accomplish this, gas pressure is increased to overcome the metallostatic pressure head of the melt and purge the prior metal sample from chamber 34 through orifice 40. This increased gas pressure and flow also purges residual aerosol from the system through conduit 62. Probe 70 is then moved to the desired location, and the gas pressure in chamber 34 is adjusted in accordance with the invention to introduce a new sample of molten metal into chamber 34. This new sample can then be analyzed in the manner previously discussed. The procedure can be repeated as desired to provide data on the homogeneity of the melt and to monitor its composition as a function of time.

The following examples are presented to provide a more complete understanding of the invention. The specific techniques conditions, materials, proportions and reported data set forth to illustrate the principles of the invention are exemplary and should not be construed as limiting the scope of the invention.

EXAMPLE 1

An iron base alloy was melted in a crucible and the constituent elements were measured with an insitu probe. The probe was comprised of a hollow cylindrical outer housing and a tubular inner housing located concentrically therewith. A spark electrode was fixedly positioned concentric with the inner housing and extended downward past the bottom end of the inner housing. The outer housing extended downward past the end of the spark electrode. This configuration did not provide a means for precisely setting the spark gap between the end of the spark electrode and the surface of a molten conductive liquid introduced into the outer housing. A pressurized gas flow was directed in through the inner housing and past the end of the spark electrode. The pressurized gas flow then travelled through the annulus between the inner and outer housing and exited through an exit port, thereby carrying aerosol particles generated by a spark which was arced between the spark electrode and the free surface of the molten metal within the outer housing. The probe was lowered into a melt of an iron-base alloy and purged by bubbling gas around the end of the outer housing. The gas pressure was then reduced until the bubbling stopped and an aliquot of molten metal entered into the outer housing to a level somewhere below the end of the spark electrode. An electrical spark discharge between the aliquot and the electrode produced an aerosol of particles which was swept by the flow of pressurized gas out to an inductively coupled argon plasma. The plasma excited the aerosol particles to produce emissions at a wavelength of 375 nanometers (nm) which were characteristic of the element iron.

Figure 6:
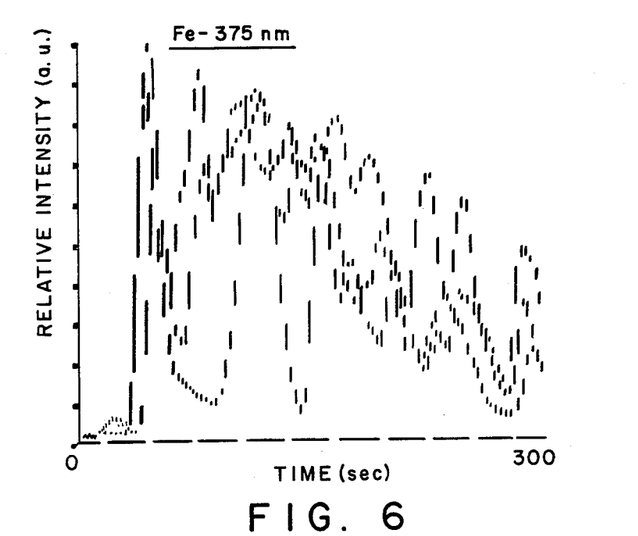
FIG. 6 shows a representative plot of analyzer output signal intensity as a function of time for a situation where the spark gap is inadequately regulated.

FIG. 6 representatively shows a plot of the relative signal intensity measured in arbitrary units (a.u.) as a function of time. A consistent, stable signal intensity could not be maintained.

EXAMPLE 2

A solder composed of 63.74 wt % Sn; 35.83 Pb; 0.2197 Sb; 0.0929 Cu; 0.0008 Zn; and 0.0047 Fe was melted in a crucible. A probe having the configuration representatively shown in FIG. 5 was employed to produce aerosol samples, and the aerosol samples were transported by a flow of gas to an inductively coupled argon plasma. The plasma excited the aerosol particles to produce emission spectra characteristic of the constituent elements of the solder. A precise spark gap was set and maintained employing the method and apparatus of the present invention.

Figure 7:
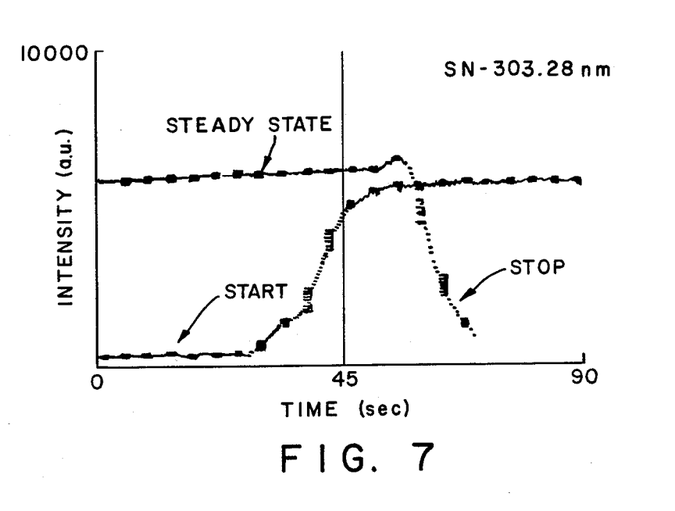
FIG. 7 shows a representative plot of analyzer signal intensity (of wavelength of 303.28 nm) as a function of time for a melt sample which contains tin (Sn)

FIG. 7 representatively shows a plot of signal intensity as a function of time for emissions at a wave length of 303.28 nanometers which are characteristic of the element tin. The "start" portion of the curve indicates the rise in signal intensity as the spark begins to generate an aerosol from the molten solder. The "steady state" portion of the plot indicates the signal intensity maintained during the course of the test analysis. The "stop" portion of the plot indicates the drop in signal intensity when the aerosol generation was ceased. The method and apparatus of the present invention were able to maintain a stable, substantially constant signal intensity which could be readily analyzed.

EXAMPLES 3 and 4

Figure 8:
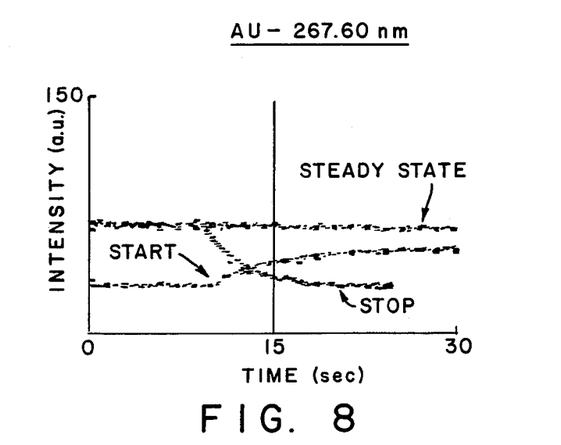
FIG. 8 shows a representative plot of signal intensity (of wavelength 267.60 nm) as a function of time for a melt which contains gold (Au)
Figure 9:
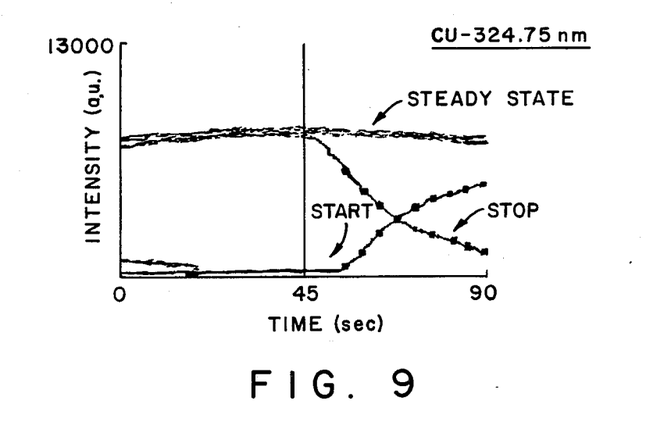
FIG. 9 shows a representative plot of signal intensity (of wavelength 324.75 nm) as a function of time for a melt which contains copper (Cu)
Figures 10A, 10B, 10C, 10D:
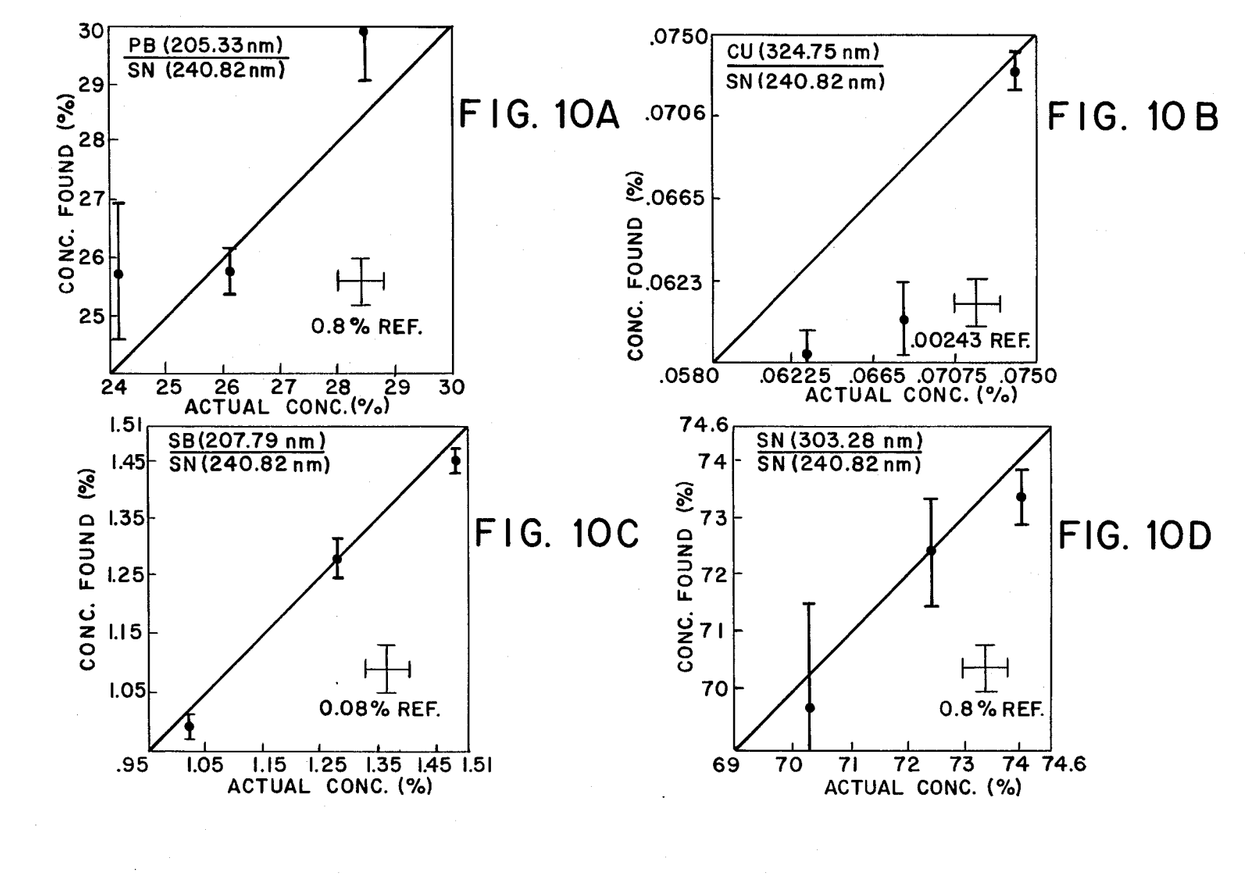
FIGS. 10A–10D show representative plots of measured concentrations as a function of actual concentrations for four elements contained in a molten solder.

FIG. 8 representatively shows a plot of signal intensity versus time for emissions at a wavelength of 267.60 nanometers which are characteristic of the element gold. FIG. 9 representatively shows a plot of signal intensity versus time for emissions at a wave length of 324.75 nanometers which are characteristic of the element copper. Multiple traces covering an extended period of several minutes can be discerned in the steady state poriton of FIG. 9. These plots were generated by using the method and apparatus of the present invention. From these plots, it is readily apparent that the method and apparatus of the invention were capable of producing a stable, steady state signal intensity at the wavelengths characteristic of the gold and copper constituents of the solder alloy.

EXAMPLES 5-8

FIGS. 10A–10D representatively show graphs of measured concentrations, in percent, as a function of actual concentrations, in percent, for the elements lead (Pb), copper (Cu), antimony (Sb) and tin (Sn).

In the course of these experiments, particular elemental components of the solder described in Example 2 were varied between the ranges set forth below:

Sn 63.74–74.14 wt %
Pb 35.83–24.20 wt %
Sb 0.2197–1.49 wt %
Cu 0.0929–0.0629 wt %

The measured concentration percents were determined by taking a ratio against an internal standard. In these examples, the ratio was taken with respect to the 240.82 nanometer wavelength line emitted by tin. The technique of taking a ratio against an internal standard compensates for fluctuations in the total signal intensity emitted from an excited sample of analyte. This technique is well known in the art.

The vertical hash marks indicate a one sigma standard deviation of the measured concentrations. The dot on the vertical hash mark indicates the midpoint within the standard deviation. The close proximity of the measured data to the diagonal line indicates that the analyses produced by using the method and apparatus of the present invention were very accurate. The small values of the standard deviation indicated that the concentration measurements were easily reproducible.

EXAMPLE 9

Figure 11:
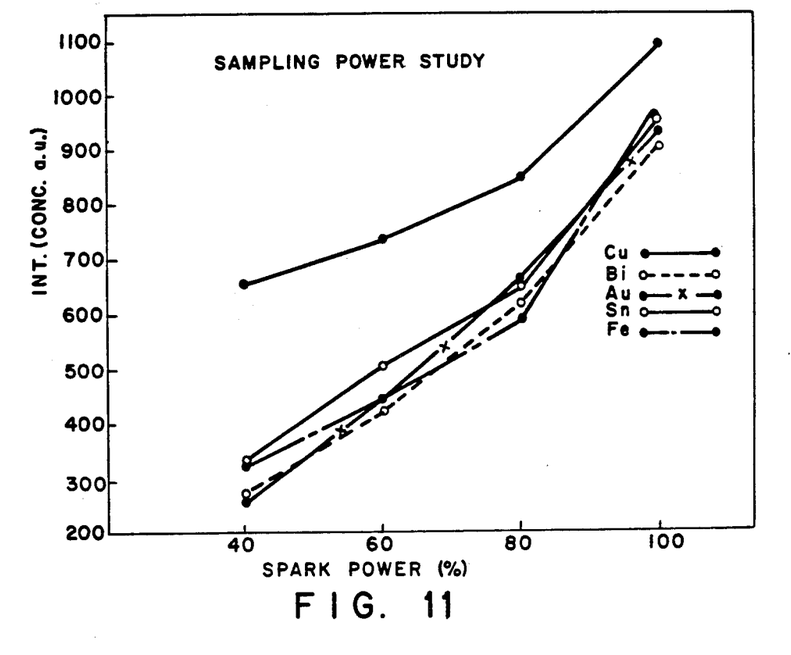
FIG. 11 is a graph which representatively shows analyzer signal intensity as a function of power supplied to the aerosol creating spark.

FIG. 11 representatively shows a graph of signal intensity as a function of spark power. Signal intensities are shown for the elements copper, bismuth, gold, tin, and iron found within a sample of molten solder alloy. The method and apparatus of the present invention advantageously provide a near linear relationship between signal intensity and spark power. The linear relationship is particularly apparent between the range of 40-80 percent spark power.

Having thus described the invention in rather full detail, it will be understood that these details need not be strictly adhered but that various changes and modifications may suggest themselves to one skilled in the art, all falling within the scope of the invention as defined by the subjoined claims.

I claim:

1. A method for sampling a liquid, electrically conductive material, comprising the steps of:
   (a) positioning an inner housing at a selected longitudinal location within a probe housing;
   (b) positioning a spark electrode at a retracted position within said inner housing, thereby spacing an electrical discharge portion of said spark electrode inward from a sampling lower end portion of said inner housing by a first selected distance;
   (c) introducing an aliquot sample of said liquid material into a sampling chamber which is delimited by said probe housing and which is in fluid communication with said inner housing sampling lower end portion and said spark electrode;
   (d) providing an atmosphere of non-reactive gas at a selected pressure in said sampling chamber;
   (e) detecting a reference liquid level at which the location of the gas contact surface of said aliquot is substantially the same as the location of the sampling lower end portion of said inner housing;
   (f) changing a relative distance between said gas contact surface and said inner housing sampling lower end portion to establish a separation position at which said inner housing sampling lower end portion is removed and spaced from said gas contact surface by a selected separation gap distance;
   (g) positioning said spark electrode within said inner housing at a work position spaced inward from the sampling lower end portion of said inner housing by a selected working distance;
   (h) sparking an electrical arc between said spark electrode and said gas contact surface of said liquid aliquot, thereby producing an aerosol sample composed of particles of said material in said gas;
   (i) providing a flow of said non-reactive gas through said sampling chamber and through the region of said electrical arc; and
   (j) directing a flow of said non-reactive gas and said aerosol sample out from said sampling chamber.

2. A method as recited in claim 1, wherein said detecting step (e) is comprised of the step of sensing the starting of flow of a gas out from the sampling lower end portion of said inner housing.

3. A method as recited in claim 1, wherein said changing step (f) is comprised of the step of decreasing a relative depth at which said probe housing is located within said liquid material.

4. A method as recited in claim 1, wherein said changing step (f) comprises the step of increasing the pressure of said non-reactive gas provided to said sampling chamber.

5. A method as recited in claim 1, wherein said detecting step (e) is comprised of the step of sensing the stoppage of flow of a gas out from the sampling lower end portion of said inner housing.

6. A sampling probe for sampling a liquid, electrically conductive material, comprising:

(a) a probe housing which delimits a sampling chamber constructed to contain a non-reactive gas;

(b) entry means for introducing an aliquot of said liquid material into said sampling chamber;

(c) an inner housing which is located within said probe housing and is moveable longitudinally relative thereto;

(d) housing adjustment means for selectively positioning said inner housing longitudinally relative to said probe housing;

(e) a spark electrode disposed within said inner housing and in communication with said sampling chamber, said electrode being longitudinally moveable relative to said inner housing and constructed to spark an electrical arc between said spark electrode and a free surface of said liquid aliquot, thereby producing an aerosol sample composed of particles of said material in said gas;

(f) spark electrode adjustment means for selectively positioning said spark electrode longitudinally relative to said inner housing to selectively locate an electrical discharge portion of said spark electrode farther from said liquid free surface than from a sampling end portion of said inner housing;

(g) gas entry means for providing an atmosphere of said non-reactive gas at a selected pressure in said sampling chamber; and (h) exit means for directing a flow of said gas and said aerosol sample out from said sampling chamber.

7. A sampling probe as recited in claim 6, wherein said inner housing is located substantially concentric with said probe housing and said spark electrode.

8. A sampling probe as recited in claim 6, wherein said housing adjustment means comprises:

(a) an inner housing top portion which is extendable past a terminal end of said probe housing and has a plurality of substantially parallel circumferential grooves formed therein; and (b) clamping means for selectively engaging said probe housing and at least one of said grooves to hold said inner housing in a selected, substantially constant position with respect to said probe housing.

9. A sampling probe as recited in claim 6, wherein said electrode adjustment means comprises:

(a) a screw-drive mechanism connected to said spark electrode and constructed to move said electrode longitudinally relative to said inner housing; and (b) measuring means for indicating the relative longitudinal position between said spark electrode and said inner housing.

10. A sampling probe as recited in claim 6, wherein said probe housing is composed of an electrically conductive material.

11. A sampling probe as recited in claim 6, wherein said probe housing is composed of an electrically conductive refractory material.

12. A sampling probe as recited in claim 11, wherein said probe housing is composed of a silicon carbide refractory material.

13. A sampling probe as recited in claim 6, further comprising:

a cooling coil located around said probe housing for cooling said probe with a flow of fluid coolant.

* * * * *